United States Patent
Joseph et al.

(10) Patent No.: US 6,171,985 B1
(45) Date of Patent: *Jan. 9, 2001

(54) LOW TRAUMA ADHESIVE ARTICLE (75) Inventors: Eugene G. Joseph, Vadnais Heights; Richard Ferber, Fridley; Donald Battles, Arden Hills; Joseph Tucker, Shoreview, all of MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/980,541

(22) Filed: Dec. 1, 1997

(51) Int. Cl.$^7$ .............................. A61F 13/00; D04H 1/54; D04H 3/12; B32B 5/26
(52) U.S. Cl. ..................... 442/346; 442/350; 442/351; 442/381; 442/394; 428/316.6; 428/317.3; 428/317.5; 602/45; 602/47; 602/54; 602/58
(58) Field of Search ................. 428/316.6, 317.5, 428/40.1, 41.3, 317.3; 424/448; 602/54, 58, 45, 47, 52, 59; 442/340, 346, 347, 350, 351, 381, 389, 394, 395, 396, 397, 398, 400, 401

(56) References Cited

U.S. PATENT DOCUMENTS

| | | | |
|---|---|---|---|
| 3,121,021 | 2/1964 | Copeland | 117/122 |
| 3,364,063 | * 1/1968 | Satas | 117/98 |
| 3,485,706 | 12/1969 | Evans | 428/134 |
| 3,825,379 | 7/1974 | Lohkamp et al. | 425/72 |
| 3,849,241 | 11/1974 | Butin et al. | 161/169 |
| 3,908,650 | * 9/1975 | Dunshee et al. | 128/156 |
| 3,954,697 | 5/1976 | McConnell et al. | 526/348.3 |
| 4,024,312 | 5/1977 | Korpman | 428/343 |
| 4,072,812 | 2/1978 | McConnell et al. | 526/348.2 |
| 4,140,115 | 2/1979 | Schnonfeld | 128/156 |
| 4,264,576 | 4/1981 | Zimmeman et al. | 424/22 |
| 4,302,500 | * 11/1981 | Flora | 428/284 |
| 4,379,201 | 4/1983 | Heilmann et al. | 428/345 |
| 4,554,324 | 11/1985 | Husman et al. | 525/301 |
| 4,595,001 | 6/1986 | Potter et al. | 128/156 |
| 4,619,979 | 10/1986 | Kotnour et al. | 526/88 |
| 4,737,559 | 4/1988 | Kellen et al. | 526/291 |

(List continued on next page.)

FOREIGN PATENT DOCUMENTS

| | | | |
|---|---|---|---|
| 0 091 800 | 4/1983 | (EP) | A61L/15/06 |
| 0 353 972 A1 | 7/1989 | (EP) | A61F/13/02 |
| 0 368 541 A1 | 11/1989 | (EP) | A61F/13/02 |
| 0 368 541 A1 | 5/1990 | (EP) | A61F/13/02 |
| 0 448 213 A2 | 2/1991 | (EP) | A61K/31/20 |
| 0 432 763 A1 | 6/1991 | (EP) | D04H/1/56 |
| 0 603 497 A1 | 10/1993 | (EP) | D04H/13/00 |

(List continued on next page.)

OTHER PUBLICATIONS

Product Information from DuPont Sontara Technologies, "Sontara Today: Applications and Properties" (undated).

*Primary Examiner*—Ellis Robinson
*Assistant Examiner*—John J. Figueroa
(74) *Attorney, Agent, or Firm*—Gary L. Griswold; Robert W. Sprague; William J. Bond (57) ABSTRACT

A low trauma pressure-sensitive adhesive coated substrate comprising a sheet material, tape or laminate structure designed to adhere to skin or like surfaces. The pressure-sensitive adhesive layer of this adhesive coated substrate is a fibrous adhesive layer generally having a basis weight of from 5 to 200 g/m$^2$ applied to a conformable backing or substrate. The fibrous adhesive layer has a textured outer face and persistent porosity between discrete adhesive fibers. Generally, the fibrous adhesive layer has a MVTR (measured by ASTM E 96–80 at 40° C.) of at least 1000 g/m$^2$/day, preferably at least 6000 g/m$^2$/day.

32 Claims, 4 Drawing Sheets

U.S. PATENT DOCUMENTS

| | | | |
|---|---|---|---|
| 4,843,134 | 6/1989 | Kotnour et al. | 526/318 |
| 5,133,355 | 7/1992 | Strand et al. | 128/640 |
| 5,153,040 * | 10/1992 | Faasse, Jr. | 428/40 |
| 5,215,087 | 6/1993 | Anderson et al. | 128/640 |
| 5,238,733 | 8/1993 | Joseph et al. | 428/284 |
| 5,276,079 | 1/1994 | Duan et al. | 524/386 |
| 5,336,219 * | 8/1994 | Krantz | 606/15 |
| 5,382,400 | 1/1995 | Pike et al. | 264/168 |
| 5,438,988 | 8/1995 | Duan et al. | 128/640 |
| 5,462,538 | 10/1995 | Korpman | 604/372 |
| 5,496,363 | 3/1996 | Burgio et al. | 607/152 |
| 5,505,200 | 4/1996 | Takaki | 128/640 |
| 5,506,279 | 4/1996 | Babu et al. | 522/34 |
| 5,520,180 | 5/1996 | Uy et al. | 128/640 |
| 5,601,851 | 2/1997 | Terakawa | 425/72.2 |
| 5,613,942 | 3/1997 | Lucast et al. | 605/52 |
| 5,614,310 | 3/1997 | Delgado et al. | 428/316.6 |
| 5,633,070 * | 5/1997 | Murayama et al. | 428/194 |
| 5,637,646 | 6/1997 | Ellis | 525/309 |
| 5,641,506 | 6/1997 | Talke et al. | 424/443 |
| 5,709,651 * | 1/1998 | Ward | 602/57 |

FOREIGN PATENT DOCUMENTS

| | | | |
|---|---|---|---|
| 0 658 351 A1 | 12/1994 | (EP) | A61L/15/58 |
| WO 96/07522 | 3/1996 | (WO) | B29B/13/02 |
| WO 96/14094 | 5/1996 | (WO) | A61L/15/58 |
| WO 97/02375 | 1/1997 | (WO) | D01F/8/06 |
| WO 97/05171 | 2/1997 | (WO) | C08F/2/22 |

* cited by examiner

LOW TRAUMA ADHESIVE ARTICLE

BACKGROUND OF THE INVENTION

The invention relates to pressure-sensitive adhesive products for use in adhering to skin or like delicate surfaces.

Pressure-sensitive adhesive tapes and the like are used in a wide variety of applications where there is a need to adhere to skin, for example, medical tapes such as wound or surgical dressings, athletic tapes, surgical drapes, or tapes or tabs used in adhering medical devices such as sensors, electrodes, ostomy appliances or the like. A concern with all these adhesive coated products is the need to balance the objective of providing sufficiently high levels of adhesion to ensure that the pressure-sensitive tape products do not fall off, while ensuring that the underlying skin experiences the least amount of trauma, damage or irritation possible while the adhesive tape or the like is being used and/or removed. These goals are generally conflicting. Pressure-sensitive adhesives are known that are hypoallergenic in nature, minimizing allergic reactions. However, tape products using these adhesives can still damage or irritate skin. For example, lack of breathability can result in overhydration and sometimes maceration of the skin. Adhesives which tend to build in adhesion or have excessively high levels of initial adhesion can pull off skin cells or layers, particularly when the skin cells have lost some of their cohesion due to overhydration or maceration. These problems are particularly pronounced where tapes are repeatedly adhered to a given site. Each time a tape is removed, the underlying skin experiences a traumatic event removing further skin cells or layers, which damage can accumulate faster than the body can repair it. U.S. Pat. No. 5,614,310 addresses this problem by suggesting a particular adhesive layer formed using solvent-insoluble, solvent-dispersible, acrylate-based elastomeric pressure-sensitive adhesive microspheres optionally impregnated with an antimicrobial agent. The backing used with this adhesive preferably has a moisture vapor transmission rate (MVTR) value of at least 500 g/m$^2$/day (measured using ASTM E 96–80 at 40° C.). This adhesive showed low levels of adhesion build-up to skin over time. Although acceptable for some uses, this adhesive is somewhat difficult to manufacture, still exhibits some adhesion build-up to skin over time, can cause moisture buildup, and lacks high levels of cohesion which can result in adhesive transfer to skin.

Another approach in the art to providing pressure-sensitive tapes and the like with low levels of skin irritation and/or damage has been the use of pattern coated adhesives. A discontinuous adhesive coating on a backing allows the skin to breathe, at least in the areas of the backing not coated with adhesive. This approach is disclosed in U.S. Pat. No. 4,595,001 (Potter); U.S. Pat. No. 5,613,942; EP 353972; and EP 91800. These patent documents generally teach intermittent coating of adhesives onto different backings. For example, U.S. Pat. No. 5,613,942 describes printing pressure-sensitive adhesives using a release coated calender roll process similar to Gravure printing. This patent also teaches screen printing. However, pattern coating or printing of adhesives in this manner is problematic as it generally requires solvents which are environmentally problematic and residual low molecular weight species can cause skin irritation. It would be preferred, from environmental, manufacturing (e.g. elimination of the need for expensive solvent recovery) and performance perspectives to have adhesives coatable directly from a melt phase.

EP Pat. Appln. No. 448213 addresses the problem of skin irritation by proposing coating the skin with retinoids either prior to applying the adhesive tape or by placing a retinoid layer on the adhesive layer itself However, this conditioning barrier layer can also interfere with adhesion. Similarly, U.S. Pat. No. 4,140,115 teaches use of a specific conditioning additive to an adhesive to reduce stripping of skin cells upon removal of a tape. The adhesive mass contains an unreacted polyol in an amount ranging from 4 to 20 weight percent. However, the polyol also reduces the adhesion force.

U.S. Pat. No. 4,024,312 suggests the use of an elastomeric backing which is stretched at a zero degree angle when removed resulting in the adhesive layer stretching and removing more easily. However, elastic tapes are difficult to handle and manufacture, adhesive tackifiers tend to migrate from the adhesive into the elastic backing, and it is difficult for the user to remember to remove the tape only in this one manner, which is different from how tapes are typically removed.

There remains a need for pressure-sensitive adhesive tapes that exhibit low trauma and irritation to skin in use and upon removal, particularly repeated use on the same site, regardless of the manner of removal and which are easily made from hot melt applied pressure-sensitive adhesives.

SUMMARY OF THE INVENTION

The invention relates to a low trauma pressure-sensitive adhesive coated substrate comprising a sheet material, tape or laminate structure designed to adhere to skin or like surfaces. The pressure-sensitive adhesive layer of this adhesive coated substrate is a fibrous adhesive layer generally having a basis weight of from 5 to 200 g/m$^2$ applied to a conformable backing or substrate. The fibrous adhesive layer has a textured outer face and persistent porosity between discrete adhesive fibers. Generally, the fibrous adhesive layer has a MVTR (measured by ASTM E 96–80 at 40° C.) of at least 1000 g/m$^2$/day, preferably at least 6000 g/m$^2$/day.

DESCRIPTION OF THE PREFERRED EMBODIMENTS

Figure 4:
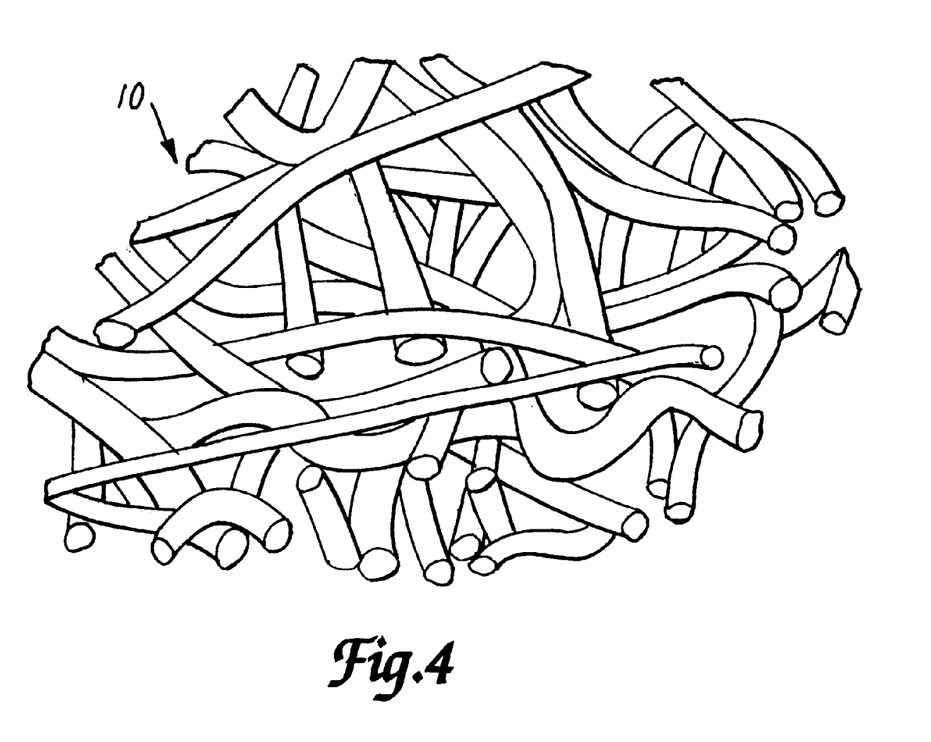
FIG. 4 is a perspective view of the breathable fibrous adhesive nonwoven web used in the invention tape.

The invention low trauma adhesive coated substrate is formed from coherent pressure-sensitive adhesive fibers which are intimately entangled each with the other in the form of a coherent breathable fibrous adhesive nonwoven web, attached to a backing. Suitable pressure-sensitive adhesive fiber webs 10 as shown in FIG. 4 can be formed as melt blown microfiber webs using the apparatus discussed, for example, in Wente, Van A., "Superfine Thermoplastic Fibers", *Industrial Engineering Chemistry*, Vol. 48, pages 1342–1346, Wente, Van A. et al., "Manufacture of Superfine Organic Fibers", Report No. 4364 of the Navel Research Laboratories, published May 25, 1954, and in U.S. Pat. Nos. 3,849,241; 3,825,379; and others. These microfine fibers are termed melt blown fibers and are generally substantially continuous and form into a coherent web between the exit die orifice and a collecting surface by entanglement of the microfibers due in part to the turbulent airstream in which the fibers are entrained. Further, suitable pressure-sensitive adhesive fibers used in the invention low trauma adhesive coated substrate can be formed by other conventional melt spinning processes, such as spunbond processes where the fibers are collected in a web form immediately upon formation. Generally, the adhesive fibers are 100 microns or less in diameter when formed by melt spinning type processes, preferably 50 microns or less.

The invention low trauma adhesive coated substrate can also comprise non-pressure-sensitive adhesive fibrous material intimately commingled with the pressure-sensitive adhesive fibers. The commingled pressure-sensitive adhesive fibers or microfibers and non-pressure-sensitive adhesive fibrous material can be present in separate individual fibers or the pressure-sensitive adhesive fibers or microfibers and the non-pressure-sensitive material can form distinct regions in a conjugate fiber and/or be part of a blend. For example, conjugate fibers can be in the form of two or more layered fibers, sheath-core fiber arrangements or in "island in the sea" type fiber structures. In this case, one component layer would comprise the pressure-sensitive adhesive fiber or microfiber and a second component layer would comprise the non-pressure-sensitive adhesive fibrous material. Generally with any form of multicomponent conjugate fibers, the pressure-sensitive adhesive fiber component will provide at least a portion of the exposed outer surface of the multicomponent conjugate fiber. Preferably, the individual components of the multicomponent conjugate fibers will be present substantially continuously along the fiber length in discrete zones, which zones preferably extend along the entire length of the fibers. The individual fibers generally are of a fiber diameter of less than 100 microns, preferably less than 50 microns or 25 microns for microfibers.

Conjugate fibers can be formed, for example, as a multilayer fiber as described, for example, in U.S. Pat. Nos. 5,238,733; 5,601,851; or PCT Publication WO 97/2375. Multilayered and sheath-core melt blown microfibers are described, for example, in U.S. Pat. No. 5,238,733, the substance of which is incorporated herein by reference in its entirety. This patent describes providing a multicomponent melt blown microfiber web by feeding two separate flow streams of polymer material into a separate splitter or combining manifold. The split or separated flow streams are generally combined immediately prior to the die or die orifice. The separate flow streams are preferably established into melt streams along closely parallel flow paths and combined where they are substantially parallel to each other and the flow path of the resultant combined multilayered flow stream. This multilayered flow stream is then fed into the die and/or die orifices and through the die orifices. Air slots are disposed on either side of a row of die orifices directing uniform heated air at high velocities at the extruded multicomponent melt streams. The hot high velocity air draws and attenuates the extruded polymeric material which solidifies after traveling a relatively short distance from the die. The high velocity air becomes turbulent between the die and the collector surface causing the melt blown fibers entrained in the airstream to mutually entangle and form a coherent nonwoven web. The either solidified or partially solidified fibers are then collected on a surface by known methods. Also, other fibers and/or particulates can be fed into this turbulent airstream thereby getting incorporated into the forming coherent nonwoven web. This can be done, for example, by using a macrodropper, a second fiber forming die or other known methods.

Alternatively, conjugate fibers can be formed by a spunbond process such as described in U.S. Pat. No. 5,382,400 where separate polymer flow streams are fed via separate conduits to a spinneret for producing conjugate fibers of a conventional design. Generally, these spinnerets include a housing containing a spin pack with a stack of plates which form a pattern of openings arranged to create flow paths for directing the separate polymer components separately through the spinneret. The spinneret can be arranged to extrude the polymer vertically or horizontally in one or more rows of fibers.

An alternative arrangement for forming melt blown conjugate fibers is described for example, in U.S. Pat. No. 5,601,851. The polymer flow streams are separately fed to each individual die orifice by the use of grooves cut in a distributing and/or separating plate. This arrangement can be used to separately extrude different polymers from different individual orifices to provide separate distinct fibers which form a coherent entangled web having a substantially uniform distribution of the differing fibers. By feeding two, separate polymers to an individual die orifice a conjugate fiber can be formed. The apparatus described is suitably used in a melt blowing type arrangement where the die orifices are formed in a row along the die.

The pressure-sensitive adhesive component comprises an extrudable pressure-sensitive adhesive suitable for melt blowing (generally this requires the adhesive to have an apparent viscosity of from 150 to 800 poise, under melt-processing conditions measured by a capillary rheometer) or other fiber spinning processes such as spunbond processing. With conjugate fibers or conformed fibers of different polymers or blends formed from a single die or spinneret, the viscosities of the separate polymer flowstreams should be fairly closely matched for uniform fiber and web formation, but this is not required. Generally matching viscosities will ensure more uniformity in the conjugate fibers formed in terms of minimizing polymer mixing, which mixing can result in fiber breakage and formation of shot (small particulate polymer material), and lower web tensile properties. However, the presence of discontinuous fibers or shot is not necessarily undesirable as long as the low trauma adhesive article has the desired overall adhesive strength.

The particular pressure-sensitive adhesive used in forming discrete pressure-sensitive adhesive fibers, conjugate fibers or blends (in either discrete or conjugate fibers) depends on the adhesive formulation in view of the desired adhesion level as taught in the invention examples and the non-pressure-sensitive adhesive material polymers selected in the case of polymer blends or conjugate fibers. The pressure-sensitive adhesive selected is generally any hot melt extrudable copolymer or composition having a viscosity in the melt phase suitable for fiber forming by melt processing. Suitable classes of pressure-sensitive adhesives include acrylate adhesives, polyalphaolefin adhesives, rubber resin adhesives or the like. Suitable rubber resin adhesives would include those formed using a tackified elastomer where a preferred elastomer is an A-B type block copolymer wherein the A blocks and B blocks are configured in linear (e.g. diblock or triblock copolymer), radial or star configurations. The A block is formed of a mono-alkenylarene, preferably a polystyrene block having a molecular weight between 4000 and 50,000, preferably between 7000 and 30,000. The A block content is preferably about 10 to 50 weight percent, preferably about 10 to 30 weight percent of the block copolymer. Other suitable A blocks may be formed from alpha-methylstyrene, t-butyl-styrene and other ring alkylated styrenes, as well as mixtures thereof The B block is formed of an elastomeric conjugated diene, generally polyisoprene, polybutadiene or copolymers thereof having an average molecular weight from about 5000 to about 500,000, preferably from about 50,000 to about 200,000. The B block dienes can also be hydrogenated. The B block content is generally 90 to 50 percent, preferably 90 to 70 percent by weight. The tackifying components for the elastomer based adhesives generally comprise solid tackifying resin and/or a liquid tackifier or plasticizer. Preferably, the tackifying resins are selected from the group of resins at least partially compatible with the polydiene B block portion of the elastomer. Although not preferred, generally a relatively minor amount of the tackifying resin can include resins compatible with the A block, which when present are generally termed end block reinforcing resins. Generally, end block resins are formed from aromatic monomer species. Suitable liquid tackifiers or plasticizers for use in the adhesive composition include napthenic oils, paraffin oils, aromatic oils, mineral oils or low molecular weight rosin esters, polyterpenes and C-5 resins. Some suitable B-block compatible solid tackifying resins include C-5 resins, resin esters, polyterpenes and the like.

The tackifier portion of the pressure-sensitive adhesive generally comprises from 20 to 300 parts per 100 parts of the elastomer phase. Preferably, this is predominately solid tackifier, however, from 0 to 25 weight percent, preferably 0 to 10 weight percent of the adhesive composition can be liquid tackifier and/or plasticizer.

Suitable rubber resin adhesives for melt blown processing are discussed in EP 658351 which exemplifies melt-blown fibrous synthetic rubber resin type adhesives used in a disposable absorbent article to either immobilize particulate sorbents or used as a pressure-sensitive adhesive attachment (e.g., for a sanitary napkin). Suitable adhesives exemplified are styrene-isoprene-styrene triblock block copolymer based, where the copolymer has coupling efficiencies ranging from 42 to 65 percent (e.g., 58 to 35 percent polystyrene-polyisoprene diblock material would be present), tackified with C-5 hydrocarbon resins (WINGTACK PLUS and WINGTACK 10 available from Goodyear) and stabilized with antioxidants.

Generally, depending on the fiber formation process, suitable antioxidants and heat stabilizers could be used in the present invention to prevent the degradation of the adhesive during the fiber forming process or in use. Also, other conventional additives could be used such as UV absorbents, pigments, particulates, staple fibers or the like.

Suitable poly(acrylates) are derived from: (A) at least one monofunctional alkyl (meth)acrylate monomer (i.e., alkyl acrylate and alkyl methacrylate monomer); and (B) at least one monofunctional free-radically copolymerizable reinforcing monomer. The reinforcing monomer has a homopolymer glass transition temperature ($T_g$) higher than that of the alkyl (meth)acrylate monomer and is one that increases the glass transition temperature and modulus of the resultant copolymer. Monomers A and B are chosen such that a copolymer formed from them is extrudable and capable of forming fibers. Herein, "copolymer" refers to polymers containing two or more different monomers, including terpolymers, tetrapolymers, etc.

Preferably, the monomers used in preparing the pressure-sensitive adhesive copolymer fibers of the present invention include: (A) a monofunctional alkyl (meth)acrylate monomer that, when homopolymerized, generally has a glass transition temperature of no greater than about 0° C.; and (B) a monofunctional free-radically copolymerizable reinforcing monomer that, when homopolymerized, generally has a glass transition temperature of at least about 10° C. The glass transition temperatures of the homopolymers of monomers A and B are typically accurate to within ±5° C. and are measured by differential scanning calorimetry.

Monomer A, which is a monofunctional alkyl acrylate or methacrylate (i.e., (meth)acrylic acid ester), contributes to the flexibility and tack of the copolymer. Preferably, monomer A has a homopolymer $T_g$ of no greater than about 0° C. Preferably, the alkyl group of the (meth)acrylate has an average of about 4 to about 20 carbon atoms, and more preferably, an average of about 4 to about 14 carbon atoms. The alkyl group can optionally contain oxygen atoms in the chain thereby forming ethers or alkoxy ethers, for example. Examples of monomer A include, but are not limited to, 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate. Other examples include, but are not limited to, poly-ethoxylated or -propoxylated methoxy (meth)acrylate (i.e., poly (ethylene/propylene oxide) mono-(meth)acrylate) macromers (i.e., macromolecular monomers), polymethylvinyl ether mono(meth)acrylate macromers, and ethoxylated or propoxylated nonyl-phenol acrylate macromers. The molecular weight of such macromers is typically about 100 grams/mole to about 600 grams/mole, and preferably, about 300 grams/mole to about 600 grams/mole. Combinations of various monofunctional monomers categorized as an A monomer can be used to make the copolymer used in making the fibers of the present invention.

Monomer B, which is a monofunctional free-radically copolymerizable reinforcing monomer; increases the glass transition temperature of the copolymer. As used herein, "reinforcing" monomers are those that increase the modulus of the adhesive, and thereby its strength. Preferably, monomer B has a homopolymer $T_g$ of at least about 10° C. More preferably, monomer B is a reinforcing monofunctional (meth)acrylic monomer, including an acrylic acid, a methacrylic acid, an acrylamide, and an acrylate. Examples of monomer B include, but are not limited to, acrylamides, such as acrylamide, methacrylamide, N-methyl acrylamide, N-ethyl acrylamide, N-methylol acrylamide, N-hydroxyethyl acrylamide, diacetone acrylamide, N,N-dimethyl acrylamide, N,N-diethyl acrylamide, N-ethyl-N-aminoethyl acrylamide, N-ethyl-N-hydroxyethyl acrylamide, N,N-dimethylol acrylamide, N,N-dihydroxyethyl acrylamide, t-butyl acrylamide, dimethylaminoethyl acrylamide, N-octyl acrylamide, and 1,1,3,3-tetramethylbutyl acrylamide. Other examples of monomer B include acrylic acid and methacrylic acid, itaconic acid, crotonic acid, maleic acid, fumaric acid, 2,2-(diethoxy)ethyl acrylate, hydroxyethyl acrylate or methacrylate, 2-hydroxypropyl acrylate or methacrylate, methyl methacrylate, isobutyl acrylate, n-butyl methacrylate, isobornyl acrylate, 2-(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl pyrrolidone, and N-vinyl caprolactam. Combinations of various reinforcing monofunctional monomers categorized as a B monomer can be used to make the copolymer used in making the fibers of the present invention.

The acrylate copolymer is preferably formulated to have a resultant $T_g$ of less than about 25° C. and more preferably, less than about 0° C. Such acrylate copolymers preferably include about 60 parts to about 98 parts per hundred of at least one alkyl (meth)acrylate monomer and about 2 parts to about 40 parts per hundred of at least one copolymerizable reinforcing monomer. Preferably, the acrylate copolymers have about 85 parts to about 98 parts per hundred or at least one alkyl (meth)acrylate monomer and about 2 parts to about 15 parts of at least one copolymerizable reinforcing monomer.

A crosslinking agent can be used if so desired to build the molecular weight and the strength of the copolymer, and hence improve the integrity and shape of the fibers. Preferably, the crosslinking agent is one that is copolymerized with monomers A and B. The crosslinking agent may produce chemical crosslinks (e.g., covalent bonds). Alternatively, it may produce physical crosslinks that result, for example, from the formation of reinforcing domains due to phase separation or acid base interactions. Suitable crosslinking agents are disclosed in U.S. Pat. Nos. 4,379,201 (Heilman), 4,737,559 (Kellen), 5,506,279 (Babu et al.), and 4,554,324(Husman).

This crosslinking agent is preferably not activated towards crosslinking until after the copolymer is extruded and the fibers are formed. Thus, the crosslinking agent can be a photocrosslinking agent, which, upon exposure to ultraviolet radiation (e.g., radiation having a wavelength of about 250 nanometers to about 400 nanometers), causes the copolymer to crosslink. Preferably, however, the crosslinking agent provides crosslinking, typically, physical crosslinking, without further processing. Physical crosslinking can occur through phase separation of domains which produces thermally reversible crosslinks. Thus, acrylate copolymers prepared from a crosslinker that provides reversible physical crosslinking are particularly advantageous in the preparation of fibers using a melt process.

Preferably, the crosslinking agent is (1) an acrylic crosslinking monomer, or (2) a polymeric crosslinking material having a copolymerizable vinyl group. More preferably the crosslinking agent is a polymeric material having a copolymerizable vinyl group. Preferably, each of these monomers is a free-radically polymerizable crosslinking agent capable of copolymerizing with monomers A and B. Combinations of various crosslinking agents can be used to make the copolymer used in making the fibers of the present invention. It should be understood, however, that such crosslinking agents are optional.

The acrylic crosslinking monomer is preferably one that is copolymerized with monomers A and B and generates free radicals in the polymer backbone upon irradiation of the polymer. An examples such a monomer is an acrylated benzophenone as described in U.S. Pat. No. 4,737,559 (Kellen et al.).

The polymeric crosslinking materials that have a copolymerizable vinyl group is preferably represented by the general formula X—(Y)$_n$—Z wherein: X is a copolymerizable vinyl group; Y is a divalent linking group where n can be zero or one; and Z is a monovalent polymeric moiety having a T$_g$ greater than about 20° C. and a weight average molecular weight in the range of about 2,000 to about 30,000 and being essentially unreactive under copolymerization conditions. Particularly preferred vinyl-terminated polymeric monomers useful in making the microfibers of the present invention are further defined as having: an X group which has the formula HR$^1$C=CR$^2$— wherein R$^1$ is a hydrogen atom or a COOH group and R$^2$ is a hydrogen atom or a methyl group; a Z group which has the formula —{C(R$^3$)(R$^4$)—CH$_2$}$_n$—R$^5$ wherein R$^3$ is a hydrogen atom or a lower (i.e., C$_1$–C$_4$) alkyl group, R$^5$ is a lower alkyl group, n is an integer from 20 to 500, and R$^4$ is a monovalent radical selected from the group consisting of —C$_6$H$_4$R$^6$ and —CO$_2$R$^7$ wherein R$^6$ is a hydrogen atom or a lower alkyl group and R$^7$ is a lower alkyl group.

Such vinyl-terminated polymeric crosslinking monomers are sometimes referred to as macromolecular monomers (i.e., "macromers"). Once polymerized with the (meth) acrylate monomer and the reinforcing monomer, a vinyl-terminated polymeric monomer of this type forms a copolymer having pendant polymeric moieties which tend to reinforce the otherwise soft acrylate backbone, providing a substantial increase in the shear strength of the resultant copolymer adhesive. Specific examples of such crosslinking polymeric materials are disclosed in U.S. Pat. No. 4,554,324 (Husman et al.).

If used, the crosslinking agent is used in a effective amount, by which is meant an amount that is sufficient to cause crosslinking of the pressure-sensitive adhesive to provide the desired final adhesion properties to the substrate of interest. Preferably, if used, the crosslinking agent is used in an amount of about 0.1 part to about 10 parts, based on the total amount of monomers.

If a photocrosslinking agent has been used, the adhesive in the form of fibers can be exposed to ultraviolet radiation having a wavelength of about 250 nm to about 400 nm. The radiant energy in this preferred range of wavelength required to crosslink the adhesive is about 100 milliJoules/centimeter$^2$ (mJ/cm$^2$) to about 1,500 mJ/cm$^2$, and more preferably, about 200 mJ/cm$^2$ to about 800 mJ/cm$^2$.

The acrylate pressure-sensitive adhesives of the present invention can be synthesized by a variety of free-radical polymerization processes, including solution, radiation, bulk, dispersion, emulsion, and suspension polymerization processes. Bulk polymerization methods, such as the continuous free radical polymerization method described in U.S. Pat. Nos. 4,619,979 or 4,843,134 (both to Kotnour et al.), the essentially adiabatic polymerization methods using a batch reactor described in U.S. Pat. No. 5,637,646 (Ellis), and the methods described for polymerizing packaged pre-adhesive compositions described in International Patent Application No. WO 96/07522, may also be utilized to prepare the polymer used in the preparation of the fibers of the present invention.

The acrylate pressure-sensitive adhesive compositions of the present invention can include conventional additives such as tackifiers (wood rosin, polyesters, etc.), plasticizers, flow modifiers, neutralizing agents, stabilizers, antioxidants, fillers, colorants, and the like, as long as they do not interfere in the fiber-forming melt process. Initiators that are not copolymerizable with the monomers used to prepare the acrylate copolymer can also be used to enhance the rate of polymerization and/or crosslinking. These additives are incorporated in amounts that do not materially adversely affect the desired properties of the pressure-sensitive adhesives or their fiber-forming properties. Typically, they can be mixed into these systems in amounts of about 0.05 weight percent to about 25 weight percent, based on the total weight of the composition.

Suitable polyolefin adhesives would include tackified polyolefin elastomer type adhesives, or amorphous polyalphaolefin polymers suitable for forming hot melt pressure-sensitive adhesives with or without added tackifier. Such amorphous polyalphaolefins are generally copolymers of a C$_3$ to C$_5$ linear alpha-olefin(s) and a higher alpha-olefin(s) (generally C$_6$ to C$_{10}$). Preferred are copolymers of polyolefins with polyhexene, polyheptene, polyoctene, polynonene and/or polydecene. Such amorphous polyalphaolefins are described in U.S. Pat. Nos. 4,264,576; 3,954,697 and 4,072,812 where the amorphous polyalphaolefin copolymers can be used without added tackifiers to directly form a pressure-sensitive adhesive. These amorphous copolymers generally have from 40 to 60 mole percent of the higher alphaolefin comonomer(s). However, suitable compatible tackifying resins and plasticizing oils can be used which generally correspond to those used to tackify the synthetic AB block copolymer elastomers described above. For example, suitable compatible liquid or solid tackifiers would include hydrocarbon resins, such as polyterpenes, C-5 hydrocarbon resins, or polyisoprenes, also resin esters of aromatic or aliphatic acids would be suitable. If these tackifiers are used in sufficient amounts, the higher alphaolefin content can be as low as 15 mole percent and still suitable pressure-sensitive adhesives can be formed.

Suitable non-adhesive materials for use in forming conjugate fibers, for use in blends with the pressure-sensitive adhesive or for use as separate fibers, include polyolefins, polyesters, polyalkylenes, polyamides, polystyrenes, polyarylsulfones, polydienes or polyurethanes; these materials are preferably extensible or slightly elastomeric, but could be elastomeric. Preferred are extensible or slightly elastomeric polyolefins such as polyethylenes, polypropylenes, ethylene-propylene copolymers, ethylene/vinyl acetate copolymers, or metallocene-type polyethylenes having a density of greater than 0.87 grams/cm$^3$. Suitable elastomeric materials would include metallocene-type polyethylene copolymers (apparent density less than 0.87 grams/cm$^3$); polyurethanes (e.g., "MORTHANE") ; polyolefin elastomers (e.g., ethylene/propylene/diene elastomers); A-B block copolymers, as described above, having A blocks formed of poly (vinyl arenes) such as polystyrene and B blocks formed of conjugated dienes such as isoprene, butadiene, or hydrogenated versions thereof (e.g., "KRATON" elastomers available from Shell Chemical Co.); polyetheresters (such as "ARNITAL", available from Akzo Plastics Co.); or polyether block amides (such as "PEBAX", available from Atochem Co.). Blends of elastomers, blends of nonelastomers or blends of both elastomers and nonelastomers can also be used for the non-pressure-sensitive adhesive fibers, conjugate fibers or in suitable blend fibers.

The non-pressure-sensitive adhesive material in fibrous form generally comprises 0 to 50 percent of the basis weight of the fibers in the fibrous adhesive web, preferably 0 to 15 percent. The non-pressure-sensitive fibrous material if present solely in the form of a blend with the pressure-sensitive adhesive material is preferably from 0 to 40 percent of the basis weight of the fibers forming the low trauma adhesive coated substrate, preferably of the substantially continuous fibers forming the low trauma adhesive coated substrate. The use of the non-adhesive material with the pressure-sensitive adhesive material decreases adhesion, however, it can also increase breathability. Where the non-pressure-sensitive adhesive fibrous material is present as a discrete fiber, these fibers are generally intimately commingled with the pressure-sensitive adhesive fibers. If the non-pressure-sensitive fibrous component is present as commingled fibers, these fibers can be formed from the same die as per U.S. Pat. No. 5,601,851 above, or in a separate die which could direct the non-pressure-sensitive adhesive fibers directly, or subsequently, into the fiber stream containing the pressure-sensitive adhesive fibers prior to collection of either fiber on a collection surface. The use of multiple dies for forming commingled fibers is known in the art. Further commingled fibers could be added as discrete staple fibers as is known in the art. The adhesive layer generally has a basis weight of from 5 to 200 g/m$^2$, preferably 20 to 100 g/m$^2$, wherein preferably at least 50 percent of the adhesive layer is in the form of pressure-sensitive adhesive fibers, preferably 85 to 100 percent.

The backing substrate to which the fibrous adhesive is adhered can be breathable or nonbreathable, but preferably is a breathable backing such as is provided by a nonwoven web, a woven or knitted web, a porous film (e.g., provided by perforations or a microporous structure), paper or other known backings or laminates. If the fibrous adhesive backing is in the form of a laminate additional components could be used, such as absorbent layers for adhesive bandage products, casting material for immobilization devices or the like. If absorbent layers are used however, they need to be thin, coherent, and conformable and able to flex if used behind the fibrous adhesive layer. The absorbent layers preferably should not be thick absorbent batts comprised of discontinuous non-coherent fibers such as wood pulp. These thick batts have high levels of absorbency and fluid holding capacity, but this is undesirable for a medical tape where fluid drainage per unit area is very low in an area directly adhered to by a tape product. Generally, absorbent layers if used in combination with the backing should be in an area of the backing not coated with the fibrous adhesive which area is intended to cover an open wound or the like where there is active liquid drainage. The backing substrate generally is from 1 to 50 mil, preferably 4 to 30 mil when a film or consolidated nonwoven web or the like. Foam backings, lofty nonwoven, or woven or knitted backings can be considerably thicker. Generally, fibrous or foam backings have a basis weight of from 15 to 200 g/m$^2$, preferably 25 to 100 g/m$^2$. The backing substrate or laminate coated with the fibrous adhesive layer generally is conformable having a hand of less than 100 grams, preferably less than 50 grams as measured on a Thwing-Albert Handle-O-Meter™ Model No. 211-300 (Thwing-Albert Instrument Co., Philadelphia, Pa.) according to the procedures outlined in the instruction manual.

Figure 3:
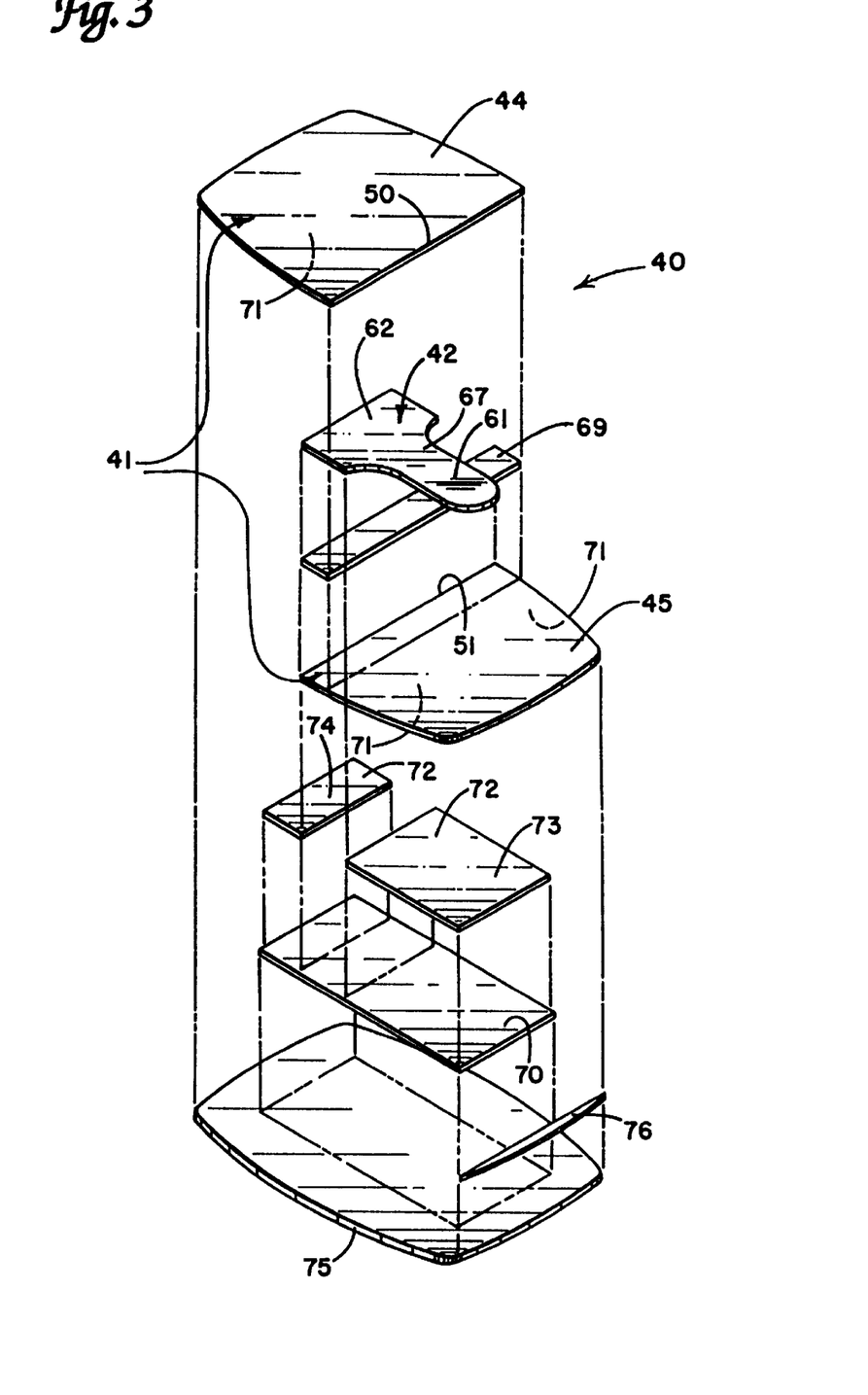
FIG. 3 is a perspective view of a biomedical electrode according to the present invention, shown in an environment of association with an electrocardiograph monitor and with a lead extending from the electrode to the monitor, phantom lines indicating a portion of the electrode hidden from view.

Another situation where the use of a low trauma adhesive coated substrates according to the present invention are particularly useful is in the construction of biomedical electrodes which are intended for long duration application and for which a high MVTR is particularly desirable. Such a construction is disclosed in U.S. Pat. No. 5,215,087 "BIOMEDICAL ELECTRODE CONSTRUCTION", which is hereby incorporated by reference. Referring now to FIG. 3, an exemplary biomedical electrode 40 after the teachings of the '087 patent is illustrated in exploded view. Electrode 40 includes an insulator construction 41, which includes first and second sections 44 and 45 which together define opposite sides 46 and 47 of the insulator construction 41. Each section 44 and 45 respectively includes an elongate edge portion 50 and 51. The insulator construction 41 is assembled from sections 44 and 45 with edge portions 50 and 51 overlapping one another.

The underside of sections 44 and 45, which together form the backing substrate of the electrode, is coated with a fibrous adhesive layer 71 to form a low trauma adhesive coated substrate according to the present invention. The preferred materials for sections 44 and 45 as disclosed in the '087 patent are melt blown polyurethanes and have a very high MVTR which are well complemented by the fibrous adhesive layers of the present invention. Other backing substrates according to the present disclosure can also be used.

The electrode 40 also includes a conductor member 42 positioned so that a tab portion 61 extends though the overlap between sections 44 and 45. A pad portion 62 of conductor member is positioned under the insulator construction 41. A double-stick strip 69 is provided to secure region 67 of the conductor member 42 in position.

A layer of conductive adhesive 70 is in contact with the pad portion 62 of the conductor member 42 to transduce electrical signals to and/or from the body of the patient and the tab portion 61, which is connected to some medical apparatus such as an electrocardiograph when the electrode 40 is in use. It is foreseen that in some embodiments the conductive adhesive 70 will be of a material which cannot be readily adhered to the fibrous adhesive layers 71, so a layer of scrim 72 may be provided, made of a material which adheres readily to the layer of conductive adhesive 70 and the fibrous adhesive layers 71. In order to allow space for the pad portion 62 to contact the conductive adhesive 70, the layer of scrim 72 may be provided in two sections, indicated at 73 and 74.

The electrode 40 is conveniently provided on a release liner 75 to protect the conductive adhesive 70 and the fibrous adhesive layer 71 until the electrode is ready to be used. A spacer 76 may be provided to facilitate peeling the electrode 40 from the release liner 75.

Other design expedients in the field of biomedical electrodes are disclosed in U.S. Pat. Nos. 5,520,180; 5,505,200; 5,496,363; 5,438,988; 5,276,079; and 5,133,355 all of which are incorporated by reference.

The low trauma adhesive coated substrate of the invention generally can be applied to a skin surface and exhibit an initial adhesion of from 20 to 100 g/2.5 cm, preferably 30 to 70 g/2.5 cm, and can be removed from the skin of a user without significant increases in Transepidermal Water Loss (TEWL, as defined in the examples). Generally, the overall TEWL after 20 tape pulls (as defined in the examples) is less than 20 g/m$^2$/hour, 0.5 hours after the last pull, where the original TEWL is generally from 3 to 7 g/m$^2$/hour. The cumulative amount of keratin removed from an area of skin after 20 pulls (as defined in the examples) from an average subject with a tape having a fibrous adhesive layer is generally less than with a tape having a continuous, hot-melt coated adhesive layer, preferably 20 percent less, and most preferably 50 percent less on average.

EXAMPLES

The following examples are offered to aid in understanding of the present invention and are not to be construed as limiting the scope thereof. Unless otherwise indicated, all parts and percentages are by weight.

TEST PROTOCOLS
Measurement of Transepidermal Water Loss (TEWL)

Evaporative water loss measurements provide an instrumental assessment of skin barrier function and skin trauma. The rate of water coming off of the skin, commonly termed Transepidermal Water Loss (TEWL), was measured with a ServoMed EP 2 Evaporimeter (Servo Med AB, Kinna, Sweden). The Evaporimeter consisted of a hand-held probe which was attached by a cable to a portable electronic display unit. At the end of the probe was an open cylinder that was 15.5 mm long and had a mean diameter of 12.5 mm. Two sensors within this open cylinder measured the temperature and relative humidity at two fixed points, approximately 4 mm apart, along the axis normal to the skin surface. This arrangement allowed the instrument to calculate an evaporative water loss, expressed in g/m$^2$/hr. The Evaporimeter was used in a test environment with a relative humidity of 35–45% and a temperature of 18–20° C. The test subject was present in such an environment for at least 15 minutes prior to measurement so that the skin reached an equilibrated state. Common TEWL values of undamaged skin are in the range of 3 to 7 g/m$^2$/hr, whereas values that range from 10 to 60 g/m$^2$/hr are indicative of damage to the epidermal skin barrier.

Keratin Assay Method

The keratin assay method was modified from that described by R. T. Tregear and P. Dirnhuber, "The Mass of Keratin Removed from the Stratum Corneum by Stripping with Adhesive Tape", *J. Investigative Dermatology*, 38: 375–381 (1961). Briefly, the method involved binding a stain in acid solution to keratin (protein) within the mass of tissue removed from the skin. Following acid washings to remove excess dye, bound dye was released from the protein with a basic solution, and the amount of dye present, determined by a spectrophotometer, was directly related to the amount of protein in the tissue. The concentration of dye in solution was compared to a standard concentration vs absorbence curve developed from a human keratin solution purchased from Sigma Chemical Company, St. Louis, Mo.

Standard Keratin Concentration Curve Preparation. One ml of water and either 0 $\mu$l, 5 $\mu$l, 10 $\mu$l, 20 $\mu$l, 40 $\mu$l, 80 $\mu$l, or 150 $\mu$l of a human keratin extract solution (Sigma, 7.7 mg/ml keratin) was placed into individual Centr/Pore (Spectrum Company, Laguna Hills, Calif.) centrifuge concentrators. One ml of dye solution (0.5 g Chromotrope FB per liter of 0.01N H$_2$SO$_4$) was then added to the keratin solution. The keratin/dye solution was allowed to stand overnight at room temperature. The tubes were then centrifuged at 2,000×g for one hour, after which the remaining solution was decanted off. One ml of 0.01N H$_2$SO$_4$ was then added to each tube and shaken vigorously. The tubes were recentrifuged for 15 minutes, solution decanted off, and the washing step repeated four more times. Following the last wash step 3 ml of 0.25N NaOH was added to each tube. The solutions were allowed to sit overnight, after which they were decanted into semi-micro cuvets and the dye concentrations determined with a spectrophotometer at a wave length of 508 nm.

Determination of Keratin on Adhesive Tapes. Two samples of known area were cut from each tape to be analyzed. The samples were placed into separate 5-ml plastic tubes. An aliquot (4.5 ml) of the dye solution was then added to each tube and the tubes allowed to sit overnight at room temperature. Each sample was washed five times with the acid solution and then an aliquot (4.5 ml) of the basic solution was added. The samples were again allowed to sit overnight at room temperature. Following the overnight extraction, all dye was removed from the tape samples and the amount of dye present was determined with the spectrophotometer as before. In calculating the concentration of keratin, the mean optical density (OD) reading of control tape (unused tape sample) was first subtracted from the test sample value and any resulting negative OD values were set at zero. Samples values were reported as $\mu$g keratin per cm$^2$ of tape.

ADHESIVE STARTING MATERIALS

Adhesive 1 (Blown Micro Fiber (BMF)-Acrylate-PSA Web)

An acrylate-based BMF-PSA web was prepared using a melt blowing process similar to that described, for example, in Wente, Van A., "Superfine Thermoplastic Fibers," in

*Industrial Engineering Chemistry*, Vol. 48, pages 1342 et seq (1956) or in Report No. 4364 of the Naval Research Laboratories, published May 25, 1954, entitled "Manufacture of Superfine Organic Fibers" by Wente, Van A.; Boone, C. D.; and Fluharty, E. L., except that the BMF apparatus utilized a single extruder which fed its extrudate to a gear pump that controlled the polymer melt flow. The gear pump fed a feedblock assembly that was connected to a melt-blowing die having circular smooth surface orifices (10/cm) with a 5:1 length to diameter ratio. The primary air was maintained at 220° C. and 241 KPa with a 0.076 cm gap width to produce a uniform web. The feedblock assembly was fed by a polymer melt stream (240° C.) comprised of isooctyl acrylate/acrylic acid/styrene macromer (IOA/AA/Sty, 92/4/4 ratio, Inherent Viscosity ~0.65 as measured by conventional means using a Cannon-Fenski #50 viscometer in a water bath controlled at 25° C. to measure the flow time of 10 ml of a polymer solution (0.2 g per deciliter polymer in ethyl acetate)) PSA, prepared as described in Example 2 of U.S. Pat. No. 5,648,166, which is incorporated herein by reference. Both the die and feedblock assembly were maintained at 220° C., and the die was operated at a rate of 178 g/hr/cm die width. The BMF-PSA web was collected on a double coated silicone release paper (Daubert Coated Products, Westchester, Ill.) which passed around a rotating drum collector at a collector to die distance of 17.8 cm. The resulting BMF-PSA web, comprising PSA microfibers having an average diameter of less than about 10–15 microns (as determined using a scanning electron microscope), had a basis weight of about 50 g/m².

Adhesive 2 (BMF-KRATON™-PSA Web)

A tackified KRATON™-based BMF-PSA web was prepared using a melt blowing process similar to that described for making Adhesive 1, except that a precompounded mixture of KRATON™ 1112 (100 parts, a styrene/isoprene/styrene block copolymer available from Shell Chemical, Houston, Tex.), ESCOREZ 1310LC (80 parts, an aliphatic hydrocarbon tackifier available from Exxon Chemical Co., Houston, Tex.) and ZONAREZ-A25 (10 parts, an alpha pinene type resin available from Arizona Chemical, Panama City, Fla.) was substituted for the IOA/AA/Sty PSA and delivered to one of the gear pumps at 190° C. The resulting BMF-PSA web had a basis weight of about 50 g/m².

Adhesive 3 (Hot-Melt Acrylate PSA Film)

The IOA/AA/Sty PSA starting material used to make Adhesive 1 was hot-melt extruded at 175° C. using a Hakke single screw extruder into a continuous film and collected between double coated silicone release liner. The resulting film had a basis weight of about 50 g/m².

Adhesive 4 (Hot-Melt KRATON™-PSA Film)

The KRATON™ PSA starting material used to make Adhesive 2 was hot-melt extruded at 160° C. using a Hakke single screw extruder into a continuous film and collected between double coated silicone release liner. The resulting film had a basis weight of about 50 g/m².

Example 1

BMF-Acrylate-PSA Tape (Polyurethane Backing)

The BMF-Acrylate-PSA web (Adhesive 1) was laminated to a melt blown polyurethane web (basis weight 100 g/m²; prepared as described in Example 1 of U.S. Pat. No. 5,230,701, which is incorporated herein by reference) using a laboratory laminator having two rubber rollers with the bottom roller temperature set at 154° C. and the top roller temperature initially at room temperature. The resulting BMF-Acrylate-PSA tape was cut into 2.5 cm×7.6 cm samples which were later used in skin trauma evaluations.

Example 2

BMF-Acrylate-PSA Tape (Rayon Backing)

The BMF-Acrylate-PSA web (Adhesive 1) was laminated as described in Example 1 to nonwoven viscose-rayon web (prepared as described in Example 1 of U.S. Pat. No. 3,121,021, which is incorporated herein by reference). The resulting BMF-Acrylate-PSA tape was cut into 2.5 cm×7.6 cm samples which were later used in skin trauma evaluations.

Example 3

BMF-KRATON™-PSA Tape (Rayon Backing)

The BMF-KRATON™-PSA web (Adhesive 2) was laminated as described in Example 1 to a nonwoven viscose-rayon web. The resulting BMF-KRATON™-PSA tape was cut into 2.5 cm×7.6 cm samples which were later used in skin trauma evaluations.

Comparative Example 1

Hot-Melt Acrylate-PSA Tape (Polyurethane Backing)

The continuous hot melt Acrylate-PSA film (Adhesive 3) was laminated as described in Example 1 to a melt blown polyurethane web. The resulting hot-melt Acrylic-PSA tape was cut into 2.5 cm×7.6 cm samples which were later used in skin trauma evaluations.

Comparative Example 2

Hot-Melt Acrylate-PSA Tape (Rayon Backing)

The continuous hot melt Acrylate-PSA film (Adhesive 3) was laminated as described in Example 1 to a nonwoven viscose-rayon web. The resulting hot-melt Acrylic-PSA tape was cut into 2.5 cm×7.6 cm samples which were later used in skin trauma evaluations.

Comparative Example 3

Hot-Melt KRATON™ PSA Tape (Rayon Backing)

The continuous hot melt KRATON™-PSA film from Example 4 was laminated as described in Example 1 to a nonwoven viscose-rayon web. The resulting hot-melt KRATON™-PSA tape was cut into 2.5 cm×7.6 cm samples which were later used in skin trauma evaluations.

SKIN TRAUMA EVALUATIONS

TEWL Measurements (Evaluation A)

A total of thirty tape samples of both the BMF-Acrylate-PSA tape with polyurethane backing (from Example 1) and the hot-melt Acrylate-PSA tape with polyurethane backing (from Comparative Example 1 ) were applied to a subject's bare-skin back over a three-day period. On day 1, ten hot-melt PSA tape samples were sequentially applied to Test Site A, each rolled down with a 2.3-kg roller four times (two cycles), and each removed immediately. Similarly, ten BMF-PSA tape samples were applied, rolled, and removed from Test Site B. The application of tape samples was then repeated on day two and day three. Test Site C was a control to which no tape samples were applied. After each of the ten tape pulls on each of the three days, TEWL was determined with a Servo Med Evaporimeter as described in the Test Protocols. A summary of results is provided in Table A.

TABLE A

| | TEWL (g/m²/hr) | | | |
|---|---|---|---|---|
| Test Site (Tape Sample) | Day 1 (6 hr after 10th tape pull) | Day 2 (0.5 hr after 20th tape pull) | Day 3 (Just prior to tape application) | Day 3 (0.5 hr after 30th tape pull) |
| A (Hot-Melt PSA) (Comparative Example 1) | 13 | 70 | 45 | 83 |
| B (BMF-PSA) (Example 1) | 7 | 9 | 10 | 15 |
| C (Control - No Tape Applied) | 6 | 7 | 6 | 8 |

These results clearly show that the amount of skin trauma caused by the BMF-Acrylate-PSA tape samples was minimal and significantly lower than the trauma caused by the hot-melt Acrylate-PSA tape samples. After ten and twenty tape pulls the BMF-PSA tape results were comparable to the Control, and only after thirty tape pulls was there a small increase in TEWL values (up to 15 g/m²/hr). In contrast, the hot-melt PSA tape results showed very large increases in TEWL values after just twenty tape pulls (up to 70 g/m²/hr) and reached a value of 83 g/m²/hr after thirty tape pulls. The results indicate that some skin healing apparently occurred overnight at the hot-melt PSA tape Site A (day-two value of 70 g/m²/hr vs day-three value, before tape application, of 45 g/m²/hr).

TEWL Measurements (Evaluation B)

Samples of both the BMF-KRATON™-PSA tape with Rayon backing (from Example 3) and the hot-melt KRATON™-PSA tape with Rayon backing (from Comparative Example 3) were applied to the bare-skin backs of two subjects (S1 and S2). In the case of Subject S1, 10 hot-melt PSA tape samples were sequentially applied to Test Site A, each rolled down with a 2.3-kg roller four times (two cycles), and each removed immediately. After four hours an 11th tape sample was similarly applied and allowed to remain in place overnight (about 18 hours). Immediately after removal of the overnight tape sample, two additional tape samples were then sequentially applied to the same Test Site and removed immediately. Similarly, a total of 13 BMF-PSA tape samples were applied, rolled, and removed from Test Site B. Test Site C was a control to which no tape samples were applied. In the case of Subject S2, the procedure was repeated exactly, except that four tape samples were applied on day two to give a total of 15 tape pulls. Initially before any tape sample was applied and four hours after the final tape pull at each Test Site, TEWL values were determined with a Servo Med Evaporimeter as described in the Test Protocols. A summary of results is provided in Table B.

TABLE B

| | TEWL (g/m²/hr) | | | | | |
|---|---|---|---|---|---|---|
| Test Site (Tape Sample) | Subject S1 | | Subject S2 | | Average | |
| | Initial | Final | Initial | Final | Initial | Final |
| A (Hot-Melt PSA) (Comparative Example 3) | 3.57 | 36.99 | 3.57 | 29.08 | 3.57 | 33.04 |
| B (BMF-PSA) (Example 3) | 4.12 | 9.00 | 2.87 | 7.30 | 3.49 | 8.15 |
| C (Control - No Tape Applied) | 3.24 | 5.48 | 3.15 | 3.55 | 3.19 | 4.52 |

These results clearly show that the amount of skin trauma caused by the BMF-KRATON™-PSA tape samples was minimal and significantly lower than the trauma caused by the hot-melt KRATON™-PSA tape samples.

Keratin Removal Measurements (Evaluation C)

Figure 1:
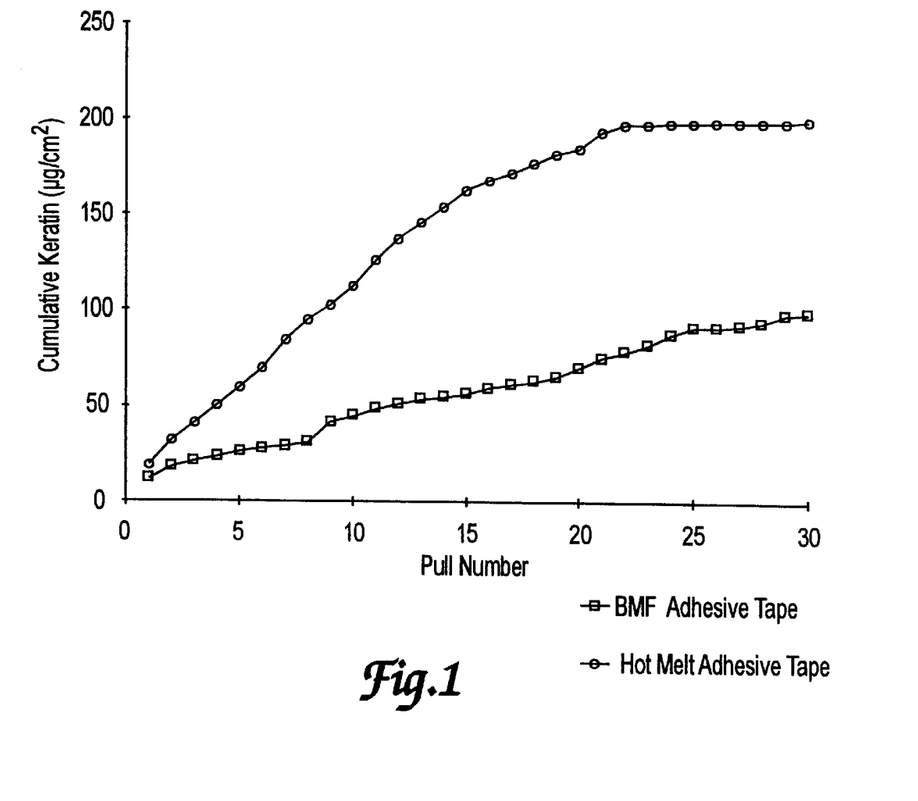
FIGS. 1 and 2 are graphs of cumulative keratin removal versus pulls of the invention tape and comparison hot melt tapes from a subject.

As part of Evaluation A described above, the cumulative keratin removed over three days (ten tape pulls/day) from Test Sites A and B was determined according to the Keratin Assay Method described in the Test Protocols. Evaluation results are shown graphically in FIG. 1. As is clearly evident from the data, a significantly greater amount of keratin was removed from Test Site A (hot-melt Acrylate-PSA Tape Site), thereby reflecting greater trauma, than was removed from Test Site B (BMF-Acrylate-PSA Tape Site).

Keratin Removal Measurements (Evaluation D)

Figure 2:
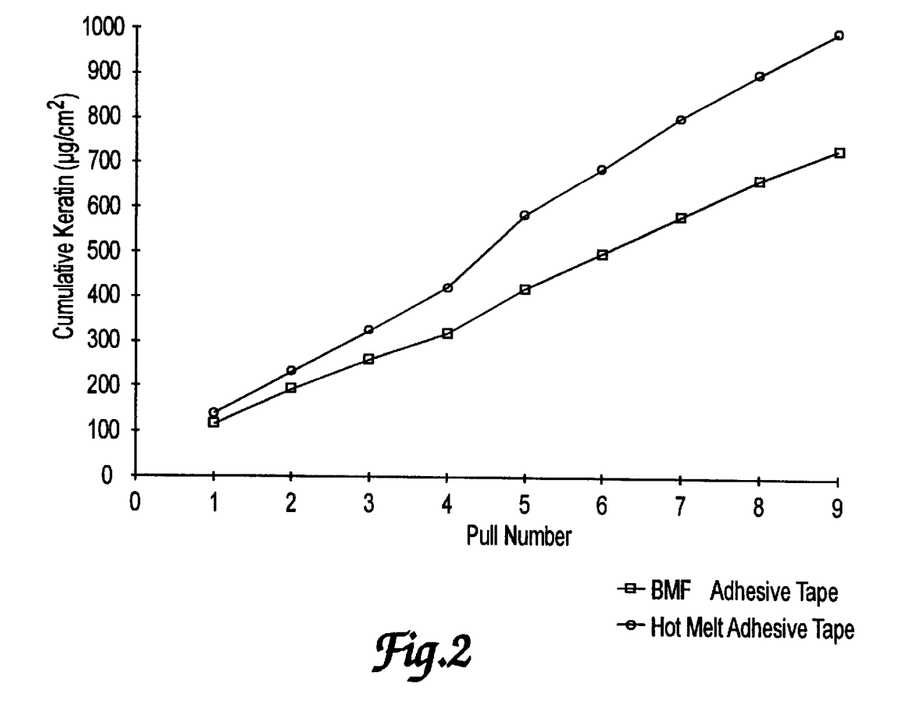

Samples of both the BMF-Acrylate-PSA tape with Rayon backing (from Example 2) and the hot-melt Acrylate-PSA tape with Rayon backing (from Comparative Example 2) were applied to a subject's bare-skin back. Nine hot-melt PSA tape samples were sequentially applied to Test Site A, each rolled down with a 2.3-kg roller four times (two cycles), and each removed immediately. Similarly, nine BMF-PSA tape samples were applied, rolled, and removed from Test Site B. The cumulative amounts of keratin removed from Test Sites A and B were then determined according to the Keratin Assay Method described in the Test Protocols. Evaluation results are shown graphically in FIG. 2. As is clearly evident from the data, a significantly greater amount of keratin was removed from Test Site A (hot-melt Acrylate-PSA Tape Site), thereby reflecting greater trauma, than was removed from Test Site B (BMF-Acrylate-PSA Tape Site).

We claim:

1. A low trauma adhesive coated substrate comprising a backing substrate and a porous fibrous adhesive layer, having a basis weight of from 5 to 200 g/m², adhesively attached to said backing substrate, said fibrous adhesive layer comprising an entangled web of discrete pressure-sensitive adhesive fibers, which pressure-sensitive adhesive fibers are adhesive along their entire length, and which pressure-sensitive adhesive fibers form an outer adhesive surface on the fibrous adhesive layer for adhesion to skin and an inner adhesive surface on the fibrous adhesive layer for adhesion to the backing substrate, which entangled web of discrete pressure-sensitive adhesive fibers has a MVTR of at least 1000 g/m²/day, provides an initial adhesion to skin of at least 20 g/2.5 cm, and provides a TEWL after 10 tape pulls per day for two consecutive days of less than 20 grams/m²/hour at 0.5 hours after the last pull (with an original TEWL of from about 3 to 7 grams/m²/hour).

2. The low trauma adhesive coated substrate of claim 1 wherein the backing substrate is breathable and the adhesive web has an MVTR of at least 6000 g/m²/day.

3. The low trauma adhesive coated substrate of claim 2 wherein the backing substrate is a nonwoven web.

4. The low trauma adhesive coated substrate of claim 2 wherein the backing substrate has a basis weight of from 15 to 200 g/m².

5. The low trauma adhesive coated substrate of claim 2 wherein the backing substrate has a basis weight of from 20 to 150 g/m².

6. The low trauma adhesive coated substrate of claim 3 wherein the backing substrate has a basis weight of from 25 to 100 g/m².

7. The low trauma adhesive coated substrate of claim 1 wherein the cumulative keratin removed from an average subject by the low trauma coated substrate is less than the cumulative keratin removed after 20 pulls by a similar substrate coated with a comparable continuous hot-melt adhesive coated substrate.

8. The low trauma adhesive coated substrate of claim 7 wherein the cumulative keratin removed from an average subject is at least 20 percent less with the low trauma adhesive coated substrate than with the comparable continuous hot-melt adhesive coated substrate.

9. The low trauma adhesive coated substrate of claim 1 wherein the backing substrate has a hand of less than 100 grams.

10. The low trauma adhesive coated substrate of claim 2 wherein the basis weight of the adhesive layer is from 20 to 100 g/m².

11. The low trauma adhesive coated substrate of claim 1 wherein the backing substrate has no liquid absorbent layers over that portion of the laminate provided with adhesive.

12. The low trauma adhesive coated substrate of claim 1 wherein the adhesive coated substrate has an initial adhesion to skin of from 20 g/2.5 cm to 100 g/2.5 cm.

13. The low trauma adhesive coated substrate of claim 1 wherein the adhesive coated substrate has an initial adhesion to skin of from 30 to 70 g/2.5 cm.

14. The low trauma adhesive coated substrate of claim 1 wherein the fibrous adhesive layer comprises commingled pressure-sensitive adhesive fibers and non-pressure-sensitive adhesive fibers.

15. The low trauma adhesive coated substrate of claim 1 wherein the pressure-sensitive adhesive fibers comprise a blend of a pressure-sensitive adhesive phase and a thermoplastic phase.

16. The low trauma adhesive coated substrate of claim 1 wherein the pressure-sensitive adhesive fibers have two or more layers along the length of the fibers at least one layer being a pressure-sensitive adhesive layer forming at least a portion of the outer surface of the fiber and at least one second layer of a thermoplastic material.

17. The low trauma adhesive coated substrate of claim 16 wherein the layers are side by side.

18. The low trauma adhesive coated substrate of claim 16 wherein the layers are concentric.

19. The low trauma adhesive coated substrate of claim 16 wherein the layers are coextensive and continuous along the length of the fiber.

20. The low trauma adhesive coated substrate of claim 19 wherein there are at least three alternating layers.

21. The low trauma adhesive coated substrate of claim 1 wherein the fibrous adhesive web is formed of melt blown pressure-sensitive adhesive fibers.

22. The low trauma adhesive coated substrate of claim 1 wherein the fibrous adhesive web is formed of spunbond pressure-sensitive adhesive fibers.

23. The low trauma adhesive coated substrate of claim 1 wherein the pressure-sensitive adhesive fibers have an average diameter of less than about 100 microns.

24. The low trauma adhesive coated substrate of claim 1 wherein the pressure-sensitive adhesive fibers are formed from a tackified rubber-resin adhesive.

25. The low trauma adhesive coated substrate of claim 24 wherein the tackified rubber-resin adhesive comprises an A-B block copolymer and a compatible resin.

26. The low trauma adhesive coated substrate of claim 1 wherein the pressure-sensitive adhesive fiber comprises a polyalphaolefin adhesive.

27. The low trauma adhesive coated substrate of claim 1 wherein the pressure-sensitive adhesive fibers comprises an acrylate pressure-sensitive adhesive.

28. A method of using an adhesive coated substrate comprising:
   a) providing a backing substrate adhesively attached to a porous fibrous adhesive layer, having a basis weight of from 5 to 200 g/m², the fibrous adhesive layer comprising an entangled web of discrete melt extrudable pressure-sensitive adhesive fibers, which pressure-sensitive adhesive fibers are adhesive along their entire length, and which pressure-sensitive adhesive fibers form an outer adhesive surface on the fibrous adhesive layer for adhesion to skin and an inner adhesive surface on the fibrous adhesive layer for adhesion to the backing substrate, which entangled web of discrete pressure-sensitive adhesive fibers has a MVTR of at least 1000 g/m²/day, and
   b) adhering the adhesive coated substrate to skin and subsequently removing the substrate such that the adhesive coated substrate provides a TEWL after 10 tape pulls per day for two consecutive days of less than 20 g/m²/hour at 0.5 hours after the last pull (with an original TEWL of about 3 to 7 g/m²/hour).

29. The method of claim 28 wherein the cumulative keratin removed from an average subject is at least 20 percent less from the fibrous adhesive coated substrate than the cumulative keratin removed from an average subject by the low trauma coated substrate is less than the cumulative keratin removed after 20 pulls by a similar substrate coated with a comparable continuous hot-melt adhesive coated substrate.

30. The method of claim 29 wherein the cumulative keratin removed from the average subject is at least 50 percent less from the fibrous adhesive coated substrate than with the comparable continuous hot-melt adhesive coated substrate.

31. The method of claim 28 wherein the adhesive coated substrate has an initial adhesion to skin of from 20 to 100 g/2.5 cm.

32. The method of claim 28 wherein the adhesive coated substrate has an initial adhesion to skin of from 30 to 70 g/2.5 cm.

* * * * *

UNITED STATES PATENT AND TRADEMARK OFFICE
CERTIFICATE OF CORRECTION

PATENT NO.     : 6,171,985 B1                                          Page 1 of 1
DATED          : January 9, 2001
INVENTOR(S)    : Joseph, Eugene G.

It is certified that error appears in the above-identified patent and that said Letters Patent is hereby corrected as shown below:

Column 2,
Line 2, after "adhesive layer itself" and before "However,", please insert -- . --

Column 4,
Line 67, after "as well as mixtures thereof" and before "The B block", please insert -- . --.

Column 12,
Line 29, please delete "Centr/Pore" and insert -- Centr/Por® --.

Signed and Sealed this

Thirtieth Day of July, 2002

*Attest:*

*Attesting Officer*

JAMES E. ROGAN
*Director of the United States Patent and Trademark Office*